(12) United States Patent
Kusens

(10) Patent No.: US 9,489,820 B1
(45) Date of Patent: *Nov. 8, 2016

(54) METHOD FOR DETERMINING WHETHER AN INDIVIDUAL LEAVES A PRESCRIBED VIRTUAL PERIMETER

(71) Applicant: CERNER INNOVATION, INC., Kansas City, KS (US)

(72) Inventor: Neil Kusens, Sherman Oaks, CA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,762

(22) Filed: Jun. 2, 2015

Related U.S. Application Data

(63) Continuation-in-part of application No. 14/084,588, filed on Nov. 19, 2013, now Pat. No. 9,159,215, and a continuation-in-part of application No. 13/543,816, filed on Jul. 7, 2012, now Pat. No. 9,129,506.

(60) Provisional application No. 61/798,964, filed on Mar. 15, 2013, provisional application No. 61/507,088, filed on Jul. 12, 2011.

(51) Int. Cl.
  *G08B 23/00* (2006.01)
  *G08B 21/22* (2006.01)

(52) U.S. Cl.
  CPC .................. *G08B 21/22* (2013.01)

(58) Field of Classification Search
  CPC ............. G08B 21/18; G08B 13/2462; G08B 21/0202; A01K 11/006; A61B 5/0022; A61B 5/0024; A61B 5/1117; G01S 5/0027

USPC ...................................... 340/573.4
  See application file for complete search history.

(56) References Cited

U.S. PATENT DOCUMENTS

| | | |
|---|---|---|
| 5,448,221 A | 9/1995 | Weller |
| 6,614,349 B1 | 9/2003 | Proctor et al. |
| 6,804,656 B1 | 10/2004 | Rosenfeld et al. |
| 7,612,679 B1 | 11/2009 | Fackler et al. |
| 7,724,147 B2 | 5/2010 | Brown |
| 7,945,457 B2 | 5/2011 | Zaleski |
| 8,273,018 B1 | 9/2012 | Fackler et al. |
| 8,529,448 B2 | 9/2013 | McNair |
| 8,565,500 B2 | 10/2013 | Neff |
| 8,620,682 B2 | 12/2013 | Bechtel et al. |
| 8,769,153 B2 | 7/2014 | Dziubinski |
| 8,917,186 B1 | 12/2014 | Grant |

(Continued)

OTHER PUBLICATIONS

Pending U.S. Application by same inventor Neil Kusens, U.S. Appl. No. 14/084,588, filed Nov. 19, 2013, entitled "Method for Determining Whether an Individual Leaves a Prescribed Virtual Perimeter".

(Continued)

*Primary Examiner* — Kerri McNally
(74) *Attorney, Agent, or Firm* — Shook, Hardy & Bacon, LLP

(57) ABSTRACT

A method and system that allows healthcare providers, hospitals, skilled nursing facilities and other persons to monitor disabled, elderly or other high-risk individuals to prevent or reduce falls and/or mitigate the impact of a fall by delivering automated notification of "at risk" behavior and falls by such an individual being monitored where assistance is required.

20 Claims, 10 Drawing Sheets

(56) References Cited

U.S. PATENT DOCUMENTS

| | | | |
|---|---|---|---|
| 2006/0145874 | A1 | 7/2006 | Fredriksson et al. |
| 2006/0261974 | A1 | 11/2006 | Albert et al. |
| 2007/0085690 | A1 | 4/2007 | Tran |
| 2007/0279219 | A1 | 12/2007 | Warriner |
| 2008/0002860 | A1 | 1/2008 | Super et al. |
| 2008/0249376 | A1 | 10/2008 | Zaleski |
| 2009/0278934 | A1* | 11/2009 | Ecker .................. G06K 9/00771 348/152 |
| 2010/0285771 | A1 | 11/2010 | Peabody |
| 2011/0018709 | A1 | 1/2011 | Kornbluh |
| 2011/0025493 | A1 | 2/2011 | Papadopoulos et al. |
| 2011/0025499 | A1 | 2/2011 | Hoy et al. |
| 2011/0087079 | A1* | 4/2011 | Aarts .................... A61B 7/003 600/300 |
| 2011/0087707 | A1 | 4/2011 | Abraham |
| 2011/0102133 | A1 | 5/2011 | Shaffer |
| 2012/0098918 | A1 | 4/2012 | Murphy |
| 2014/0191861 | A1 | 7/2014 | Scherrer |
| 2014/0365242 | A1 | 12/2014 | Neff |

OTHER PUBLICATIONS

Pending U.S. Application by same inventor Neil Kusens, U.S. Appl. No. 14/575,850, filed Dec. 18, 2014, entitled "Method and Process for Determining Whether an Individual Suffers a Fall Requiring Assistance".

Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/613,866, filed Feb. 4, 2015, entitled "Method and System for Determining Whether an Individual Takes Appropriate Measures to Prevent the Spread of Healthcare Associated Infections Along With Centralized Monitoring".

Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".

Pending U.S. Application by same inventor Neil Kusens, U.S. Appl. No. 13/543,816, filed Jul. 7, 2012, entitled "Method and Process for Determining Whether an Individual Suffers a Fall Requiring Assistance".

Pending U.S. Application by same inventor Neil Kusens, U.S. Appl. No. 14/724,969, filed May 29, 2015, entitled "Method and Process for Determining Whether an Individual Suffers a Fall Requiring Assistance".

Pending U.S. Application by same inventor Neil Kusens, U.S. Appl. No. 14/727,434, filed Jun. 1, 2015, entitled "Method for Determining Whether Enters a Prescribed Virtual Zone Using Skeletal Tracking and 3D Blob Detection".

Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".

Pending U.S. Application by same inventor Neil Kusens, U.S. Appl. No. 14/743,499, filed Jun. 18, 2015, entitled "System for Determining Whether an Individual Suffers a Fall Requiring Assistance".

Pending U.S. Application by same inventor Neil Kusens, U.S. Appl. No. 14/743,447, filed Jun. 18, 2015, entitled "System for Determining Whether an Individual Suffers a Fall Requiring Assistance".

Non-Final Office Action dated Oct. 7, 2015 in U.S. Appl. No. 14/339,397, 16 pages.

Non-Final Office Action dated Mar. 11, 2016 in U.S. Appl. No. 14/575,850, 10 pages.

\* cited by examiner

- Virtual Safety Rail
- Bed Zone
- Auto Bed Zone (Select Patient)
- Auto Bed Zone (Auto-select)
- Saved Zones
- Clear All

METHOD FOR DETERMINING WHETHER AN INDIVIDUAL LEAVES A PRESCRIBED VIRTUAL PERIMETER This application is a continuation-in-part of U.S. application Ser. No. 14/084,588, filed Nov. 19, 2013, which is a continuation-in-part of U.S. application Ser. No. 13/543,816, filed Jul. 7, 2012, which claimed priority to and the benefit of U.S. Application Ser. No. 61/507,088, filed Jul. 12, 2011 and this application also claims priority to and the benefit of U.S. Application Ser. No. 61/798,964, filed Mar. 15, 2013, all of the above applications are incorporated by reference in their entireties for all intended purposes.

1. FIELD OF THE DISCLOSURE

The present disclosure is generally directed to patient monitoring systems and particularly to a system and method for monitoring patients in a manner which prevents or reduces patient falls.

2. BACKGROUND

According to recent studies, falls are a leading cause of death among people over the age of 65 years and 10% of the fatal falls for patients over 65 years of age occur in a hospital setting. For the general population, studies estimate that patient falls occur in 1.9 to 3% of all acute care hospitalizations. Of these hospital-based falls, approximately 30% will result in a serious injury with the cost to care for these injuries estimated to reach $54.9 billion per year by 2020. Current technologies that exist to assist in the prevention of falls are limited in their capabilities. These include pressure pads on the bed that trigger an alert when no pressure is detected on the pad, pressure pads on the floor and light beams that create a perimeter with alarms going off upon interruption of the beam. The pressure pads are ineffective as they do not prevent the fall but rather alert after the fact when it is too late. Additionally they are prone to false positive alerts. The light beams are also prone to false alerts when the patient or visitor simply reaches through it or the caregiver breaks the beam while delivering medication, food, drink or conducting a procedure on the patient.

SUMMARY OF THE DISCLOSURE

The present disclosure is directed to addressing these above-described shortcomings with current technology. Generally disclosed is a novel method and system that allows healthcare providers, hospitals, skilled nursing facilities and other persons to monitor disabled, elderly or other high-risk individuals and utilize the described technology to prevent or reduce falls and/or mitigate the impact of a fall by delivering automated notification of "at risk" behavior and falls by such an individual being monitored where assistance is required.

The following non-limiting definitions are provided as aid in understanding the disclosed novel method and system:

| | |
|---|---|
| 3D Camera, Motion and Sound Sensor | An electronic device that contains one or more cameras capable of identifying individual objects, people and motion regardless of lighting conditions as well as one or more microphones to detect audio. The cameras can utilize technologies including but not limited to color RGB, CMOS sensors, infrared projectors and RF-modulated light. They may also contain microprocessors and image sensors to detect and process information both sent out and received by the various cameras. |

The electronic device calculates if there has been a change in location of the person or object of interest over a period of time. As a non-limiting example, a person's right knee can be at time T1 located at coordinates (x1, y1, z1) in a picture frame taken by the camera. At time T2 the right knee is capture by the picture frame taken by the camera at coordinates (x2, y2, z2). Based on this information, motion, speed and direction can be derived utilizing the elapsed time and comparing the two 3D coordinates over the elapsed time. As opposed to conventional motion sensors, which use captured motion to control a camera, the 3D Motion and Sound Sensor used with the method and system, uses the camera in order to compute the motion. The camera/sensors are preferably continuously on at all times during while the monitoring is occurring, regardless of whether the person or object of interest is moving or not. The 3D Camera, Motion and Sound sensor can additionally be programmed to lock on a person and can send back to the computerized monitoring system the 3D coordinates of the joints in the person's body and a skeletal outline of the person. As a non-limiting example, a person's right arm can be at time T1 located at coordinates (x1, y1, z1) in a picture frame taken by the camera. At time T2 the right arm is captured by the picture frame taken by the camera at coordinates (x2, y2, z2). Based on this information, motion, speed and direction can be derived utilizing, the elapsed time and comparing the two 3D coordinates over the elapsed time.

The camera preferably views the entire bed or a large portion of the bed or other area that the patient is resting, at (i.e. chair, couch, etc.) simply by its placement in a manner sufficient for the monitored area to be visible to the camera. Thus, the camera does not require any triggering event to cause the camera to begin recording video and/or 3D depth data or transmitting video and/or 3D depth data to the other components of the system for analysis. As the video camera is recording or otherwise transmitting video and/or 3D depth data to the other system components at all times during monitoring, the electronic device is able to immediately track, capture and/or record the monitored individual's movements at all times within the room or monitored area and will be able to provide information as to whether and when the individual begins to move or begins to get up to move.

Preferably the 3D Camera, Motion and Sound Sensor records, captures and/or streams video and/or 3D depth data. As video is technically made up of individual picture frames (i.e. 30 frames per second of video), the above reference to picture frames is referring to frames of video.

Depth sensitivity can come into play with skeletal tracking in order to minimize false alarms, as objects behind and in front of the patient can be effectively ignored. The preferred use of depth as a factor also differentiates the current monitoring system from motion/object detection systems that rely on 2D images.

The 3D Motion and Sound Sensor is located within the room of the patient being monitored and potentially just outside of the patient's room. It is connected to the computerized communication and computerized monitoring systems via a data connection (TCP/IP or comparable technology).

| | |
|---|---|
| Computerized Virtual Safety Rail Monitoring System | A computer system specifically designed and programmed to create virtual safety rails around a specific object such as a hospital bed and which monitors activity based on information received from the 3D Camera, Motion and Sound sensor(s). The computerized monitoring system will preferably be located within the patient's room and can be connected to the centralized monitoring station at the facility but can also be located at any physical location so long as a data connection (TCP/IP or comparable technology) exists between the computerized monitoring system, the computerized communication system, centralized monitoring station and/or 3D motion and sound sensor. The computerized virtual safety rail monitoring system preferably makes its determinations based on the data received by the 3D Camera, Motion and Sound sensor(s). |
| Computerized Communication System | A computer system specifically designed and programmed to facilitate communication between the monitored patient and computerized monitoring system in the event the virtual safety rails are crossed. This system may include but is not limited to amplified speakers, microphones, lights, monitors, computer terminals, mobile phones and or other technologies to allow for the electronic communication to take place. The computerized communication system will preferably be located within the patients room being monitored but certain components of the system are mobile by their nature (i.e. mobile phones, pagers, computers) and can also be located at any location so long as a data connection (TCP/IP or comparable technology) exists between the computerized monitoring system, the computerized communication system, centralized monitoring station and 3D Camera, Motion and Sound sensor. |
| System Database | A computer database that stores records of all alerts generated, notifications, confirmation requests, responses, and reconfirmation requests and any other desired information concerning a triggering event or lack of triggering event(s). |
| Centralized Monitoring Primary Display | A computer display connected to the centralized monitoring station, showing video and audio of all patient rooms connected to the centralized monitoring station. |
| Centralized Monitoring Alert Display | A computer display connected to the centralized monitoring station, showing video and audio of any patient room where an individual is deemed to have crossed a virtual safety rail at the moment such determination is made. |
| Caregiver | A relative, friend, individual, company of facility whose purpose is to provide assistance in daily living activities for individuals who are disabled, elderly or otherwise in needs of assistance. |

DETAILED DESCRIPTION OF THE INVENTION

Figure 1:
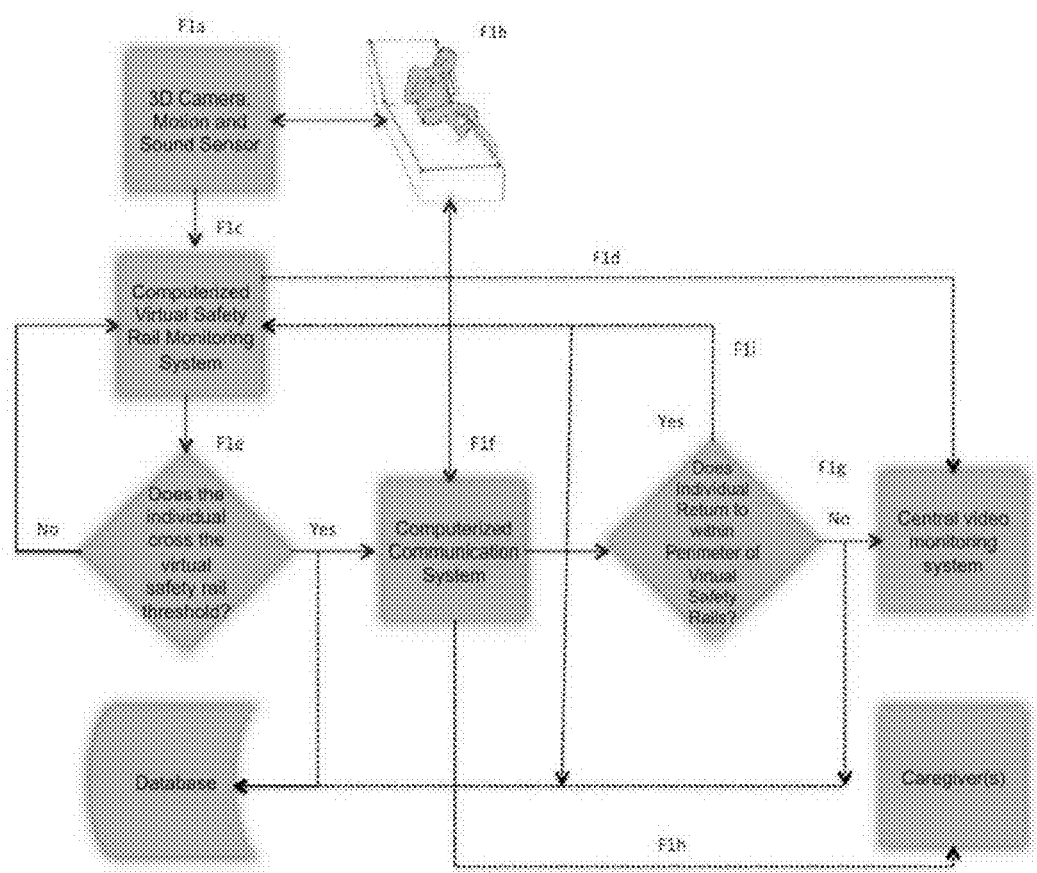
FIG. 1 is a block diagram of a virtual safety rails configuration, monitoring and alerting system and method in accordance with the present invention.

FIG. 1 illustrates a block diagram for the virtual safety rails configuration, monitoring and alerting system and method of the present invention. Specifically, FIG. 1 shows the workflow for monitoring an individual's status through the use of one or more 3D Camera, Motion and Sound sensors.

At step F1a, one or more 3D Camera, Motion and/or Sound sensors can be installed in the patient's or individual's room. At step F1b, the one or more 3D Motion and Sound sensors can be configured to recognize the individual using biometric identifiers such as height, distance between points on the body, etc. Virtual safety rails can also be calibrated at this time. At step F1c, data from the 3D Motion and Sound sensors can be sent to a. Computerized Virtual Safety Rail Monitoring System. At step F1d, a continuous video feed can be sent to the central Video Monitoring System.

At step F1e, if the computerized virtual safety rail monitoring system detects that the patient or any part of the patient has crossed outside of the designated perimeter (beyond the virtual safety rail), the monitoring system will alert the computerized communication system. A record can also be entered in a database to record the incident. If other individuals such as a caregiver are also detected at the time the virtual safety rail threshold is crossed, the system, can be designed or programmed such that no alert is generated and it will continue to monitor the data being sent from the 3D camera, motion and sound sensor. Additionally, the system can be programmed to be capable of detecting pre-programmed hand, arm, leg and body gestures from the patient/individual and/or another person in the room to initiate an alert to the computerized communication system. As a non-limiting example, a particular hand gesture could be used as a signal to send medical assistance or that the individual needs to use the restroom. Further examples are numerous.

At step F1f, the computerized communication system preferably can first issue a verbal warning to the patient that they have crossed the virtual safety rail threshold. This verbal warning can be a pre-recorded message, including, but not limited to, a pre-recorded message from any caregiver, and will advise the patient to return to within the perimeter of the virtual safety rails. At step F1g, should the patient fail to return to within the perimeter of the virtual safety rails in a timely manner, an alert can be generated on the central Video Monitoring System (see FIG. 2). The system database can also be updated to reflect actions taken. The system can be designed to provide visual and/or audio alerts.

At step F1h, the computerized communication system can notify caregivers or other designated persons that the individual requires assistance. Notification of caregivers can be made through phone call, text messaging, speakerphone systems, pagers, email, or other electronic means of communication if so desired and configured. At step F1i, if the individual returns within the perimeter of the virtual safety rails, the system database can be updated to reflect such. Additionally, the system will continue to monitor the patient and store all data in the system database.

Preferably, based on information received from the sensor(s), the computerized monitoring system can track skeletal points on a body of the specific individual being monitored in real time. The 3D Camera, Motion and Sound sensors continually capture data concerning the one or more rooms regardless of whether (and independent of) any movements or sounds have occurred in the one or more rooms. Thus, during monitoring, the 3D Camera, Motion and Sound sensors continually capture or receive data at all times and continually feed or send the data to the computerized monitoring system for processing and analysis involved in making the relevant determinations.

The monitored individual or a person/caregiver with the monitored individual can received a message from the computerized communication system which is in communication with the computerized monitoring system to determine whether or not the individual needs assistance. In one embodiment, the computerized monitoring system detects or determines that the individual may have fallen or is about to fall or crossed over a virtual safety rail, solely from the video feed forwarded from the one or more 3D Camera, Motion and Sound sensors that shows that the individual has fallen or gestured that he or she needs assistance or moved over or through the electronically defined virtual safety rail.

Figure 2:
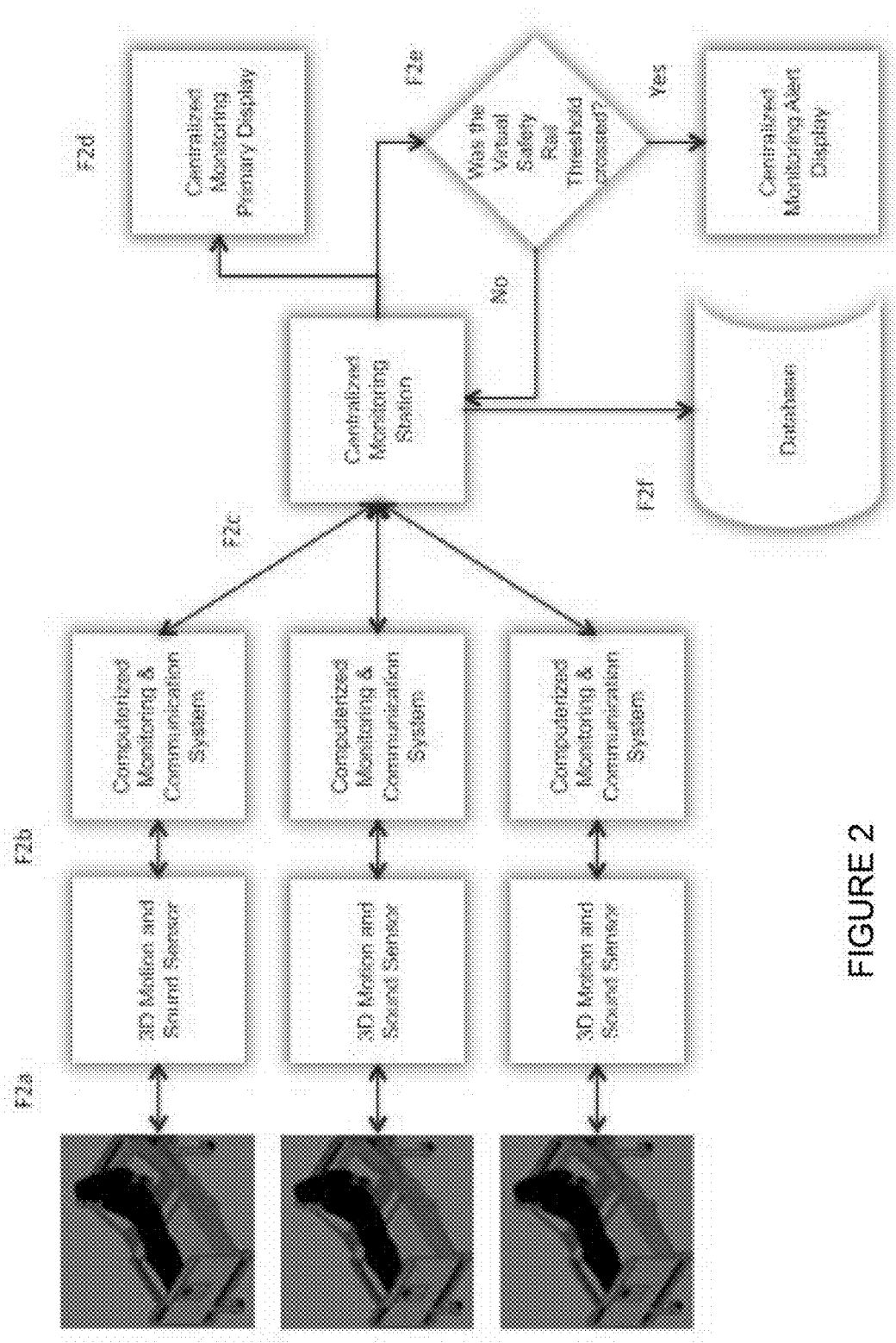
FIG. 2 is a block diagram of the centralizing monitoring and alerting system in accordance with the disclosure.

FIG. 2 illustrates a block diagram for centralized monitoring and alerting and shows the workflow for centralized monitoring and alerting of the central monitoring regarding whether an individual has crossed a virtual safety rail threshold through the use of 3D Motion and Sound sensors. At step F2a, one or more 3D Motion and Sound sensors are installed in and/or just outside an individual's room, home, hospital room, or other place of temporary or permanent residence and connected to the computerized monitoring and communication systems as described in FIG. 1. The video, audio and alert data can be sent to a centralized monitoring station where the data is aggregated. Preferably, the centralized monitoring station receives data at all times from the sensors to allow the various individuals to be constantly monitored at the centralized station regardless of whether or not a fall has been detected.

At step F2b, all video, audio and alert feeds received by the centralized monitoring station can be displayed on the centralized monitoring primary display. Alternatively, multiple centralized monitoring primary displays can be utilized based on the quantity of rooms to be monitored at a given time. At step F2c, when the centralized monitoring system receives an alert from any of the computerized monitoring and communication systems indicating that an individual in any of the monitored rooms or other locations has fallen, the video, audio and alert information is displayed on the Centralized Monitoring Alert Display. Should the centralized monitoring station receive alerts from more then one of the computerized monitoring and communication systems indicating that an individual in a monitored room or location has crossed a virtual safety rail threshold, the centralized monitoring alert display will display the video, audio and alerting information from all such instances at the same time. If no alert is received by the centralized monitoring station, nothing is displayed on the Centralized Monitoring Alert Display. At step F2d, an electronic record of any alerts received by the Centralized Monitoring Station can be stored in an electronic database, which is in communication with the Centralized Monitoring Station.

Figure 3:
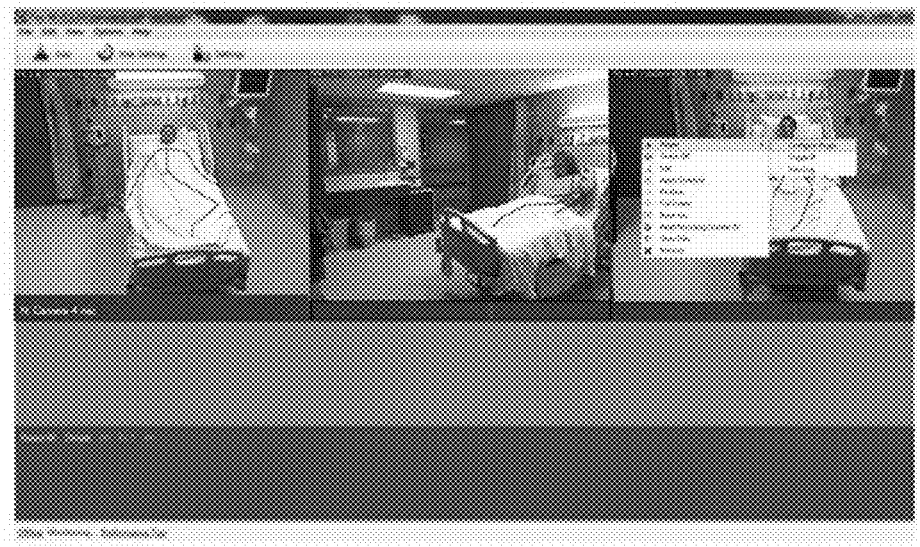
FIGS. 3 though 15 illustrate various screen shots for configuring the system for operation including defining bed zone, virtual safety rails and alert types.
Figure 4:

FIGS. 3 through 15 illustrate several set up screen shots for configuring the bed zone, virtual safety rails and alert types. In FIG. 3, the bed zone and virtual safety rails can be configured for a given or specific 3D Motion and Sound Sensor. To begin configuration, the user can hover over the 3D Motion and Sound Sensor video window with the cursor, right-click, select plugin and then select configure plug-in. A window will popup showing the 3D Motion and Sound Sensors' feed. The user selects the icon for the type of zone or rail they wish to draw, which as a non-limiting example and illustrative purposes, can be a bed zone and virtual safety rail(s) (See FIG. 4).

Figure 5:

As non-limiting examples, the icons that appear on the screen for selection can include the following symbols shown in FIG. 5. In this non-limiting example, in no particular order, some of the icons include, Bed Zone, Auto Bed Zone (Select Patient), Auto Bed Zone (Auto-select), Saved Zones, Virtual Safety Rail and Clear All.

Figure 6:
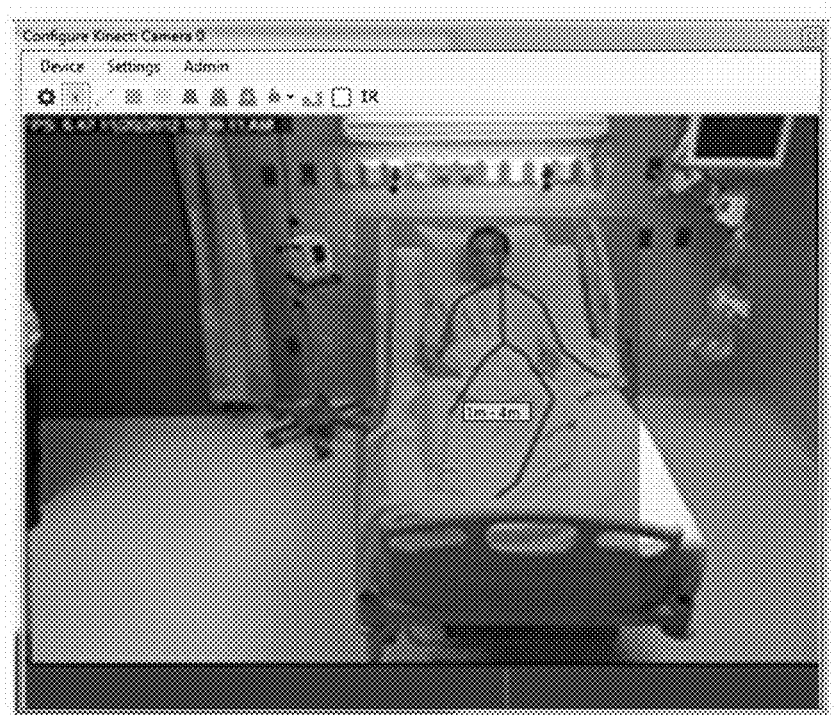
Figure 8:
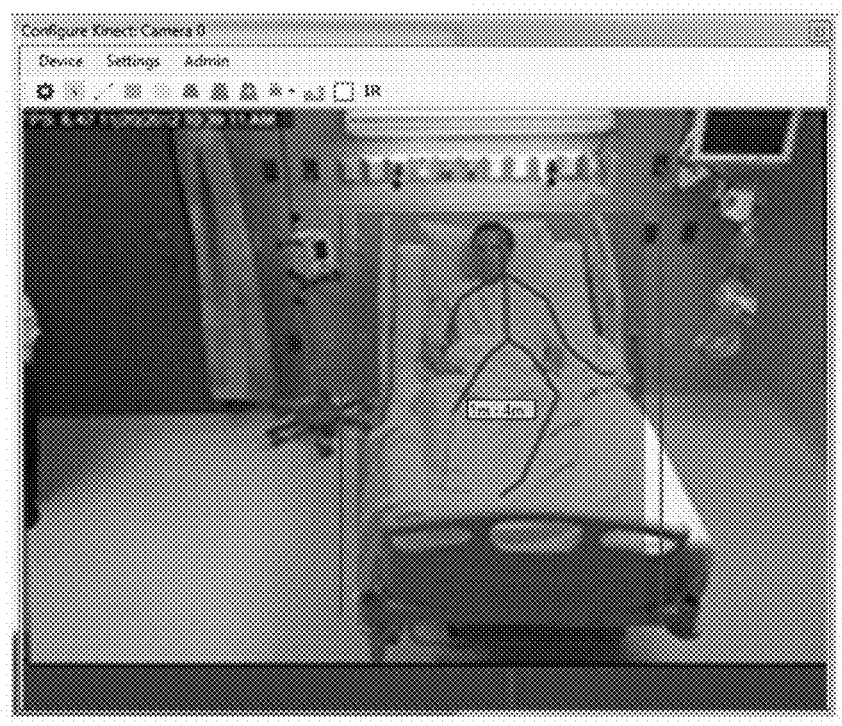

As seen in FIG. 6, to place a zone, the user clicks on the screen where he or she would like to start the zone. Then, the cursor is moved to the corner point for zone and clicked again. The user continues to select additional points until the zone is drawn to the user's satisfaction. Preferably, the user clicks on the round end point of the beginning of the zone to complete the zone (See FIG. 6). When the zone has been completed, the zone can appear and a depth range box (i.e. square, rectangle, etc. disposed over the patient on the screen) can be provided on the screen, such as, but not limited to, in the middle of the screen or zone (see FIG. 8), though any location on the screen is considered within the scope of the invention. Placing a virtual rail is done with a similar process wherein the user clicks on the screen where he or she would like to start the rail. Then the cursor is moved to the end point for the rail and the user clicks on the screen again to place the rail. As seen in FIG. 8, upon completion the zone and or rail(s) appear and has a depth range box preferably in the middle.

Figure 7:
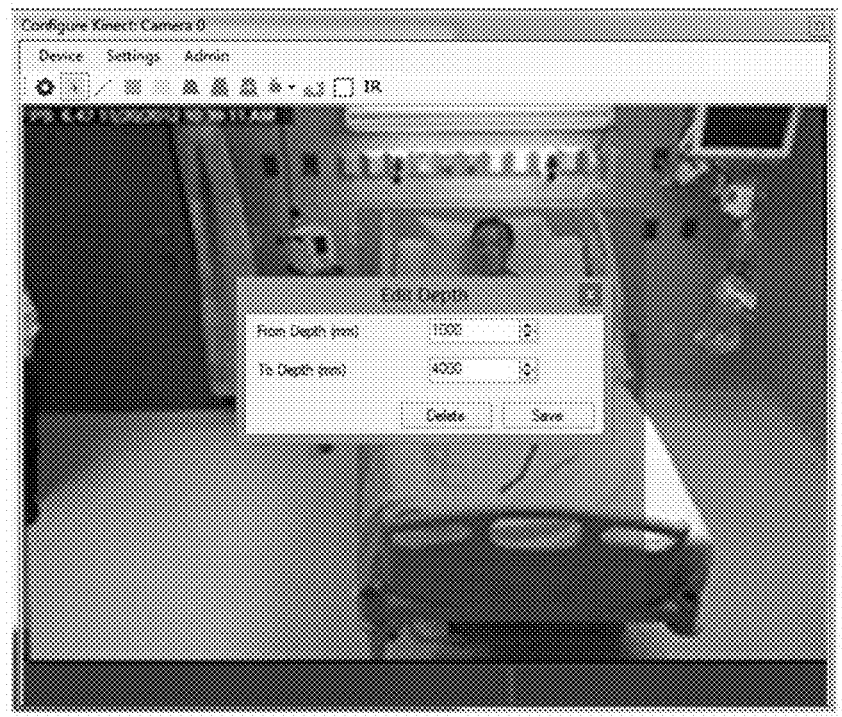

As seen in FIG. 7, the user can adjust the depth range for any given zone or rail. By preferably double clicking on the depth range box or by other conventional selection methods an Edit Depth window can appear. The user can enter in the depth ranges (preferably in millimeters (mm) though not considered limiting) and then the user can click Save button or icon when done to store the entered values.

If there are any other types of zones or rails to draw for the particular sensor, the above steps are repeated to place the next zone or rail and the depth setting can be adjusted for each if necessary. Additionally, all zones and rails can be cleared by clicking on or otherwise selecting the Clear All icon in the toolbar. Once all of the zones/rails are configured, you can close the window to finish or you have the option to save the zone/rail configuration for later use.

Figure 9:

As seen in FIG. 9, to access the main settings window, the user can click or otherwise select the Settings menu and the select Main Settings from the drop-down list. As one non-limiting alternative, the user can click on the Gear icon ( ⚙ ) or other designated icon in the toolbar to access the main settings window.

Figure 10:
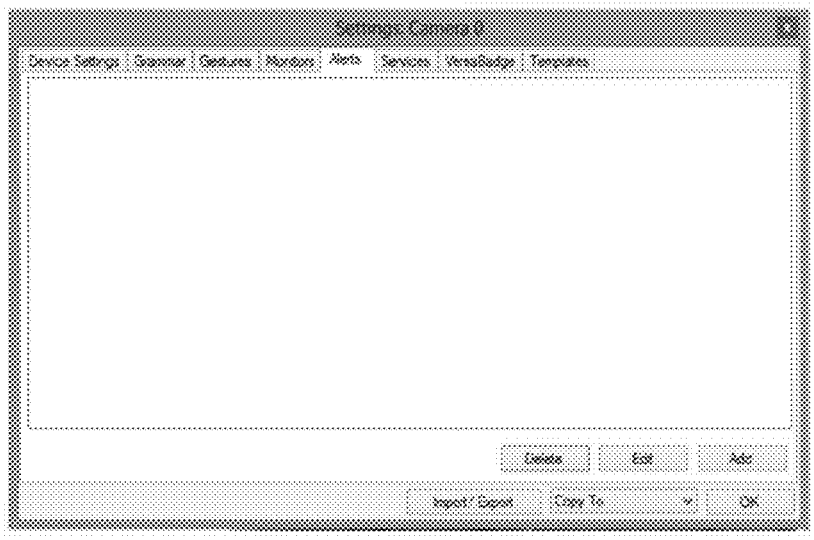
Figure 11:
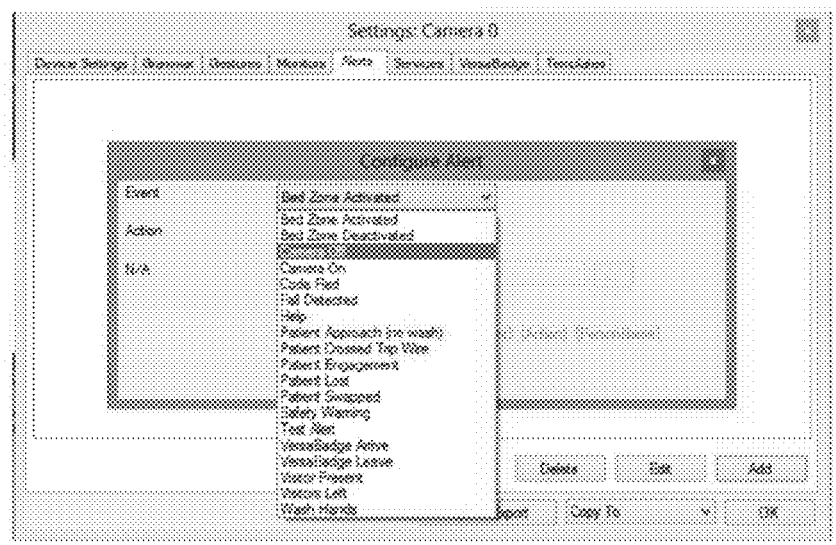

As seen in FIG. 10, for one non-limiting way to configure a new Alert, the user can select the Alerts tabs and then click on or otherwise select the Add button, which can result in the Configure Alert box appearing on the screen (See FIG. 11). As seen in FIG. 11, under the Event field, the user can then select the event from the drop down list that they wish the user wishes to send an alert on.

Figure 12:
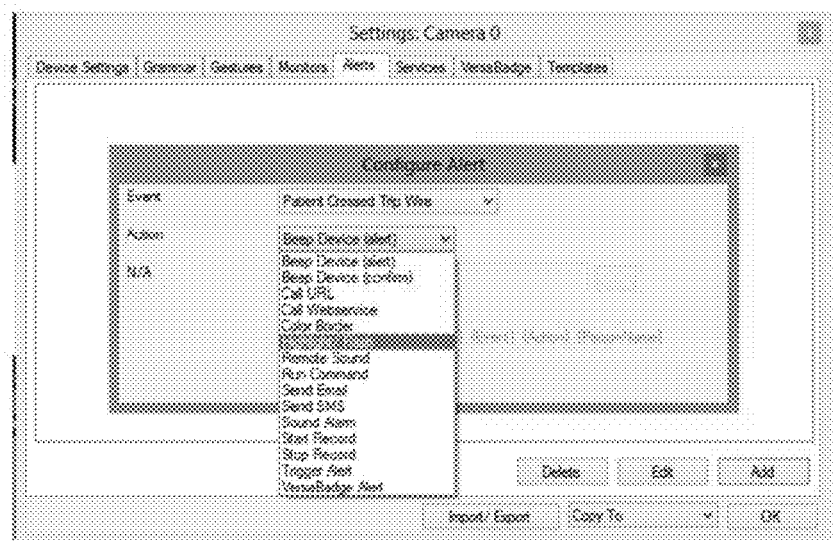
Figure 13:
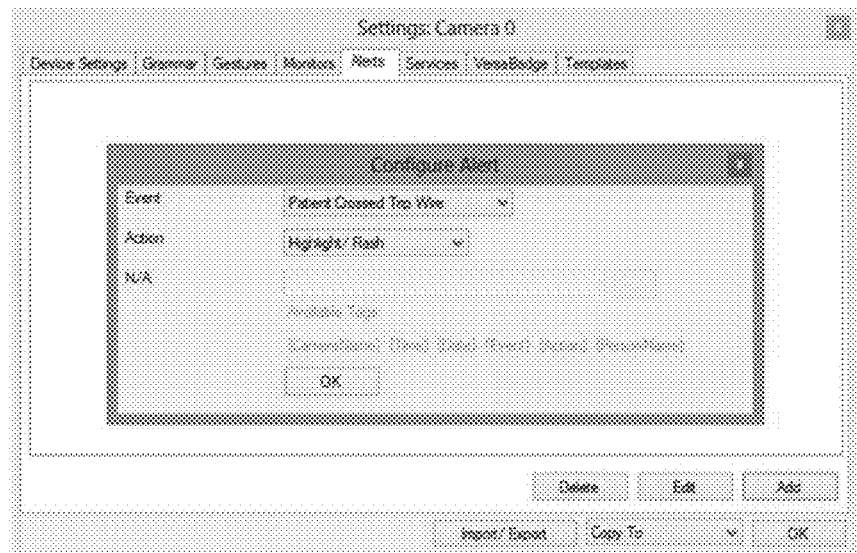
Figure 14:
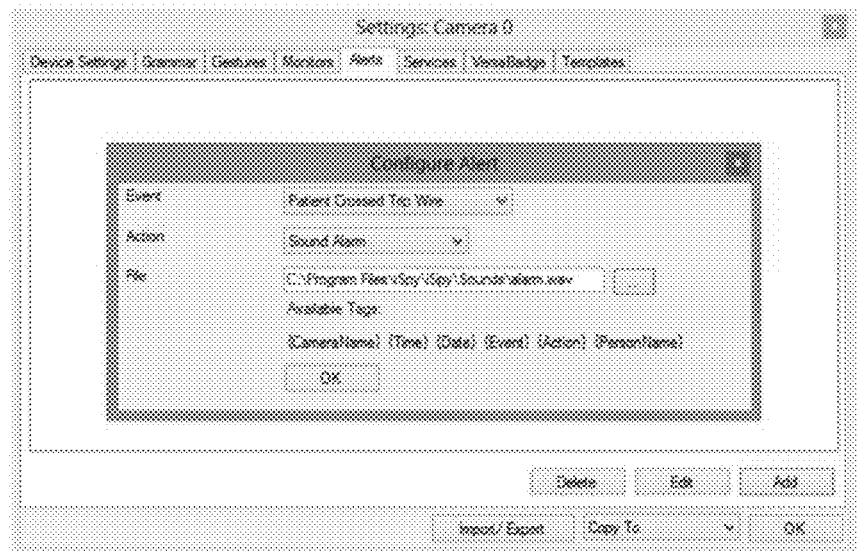
Figure 15:
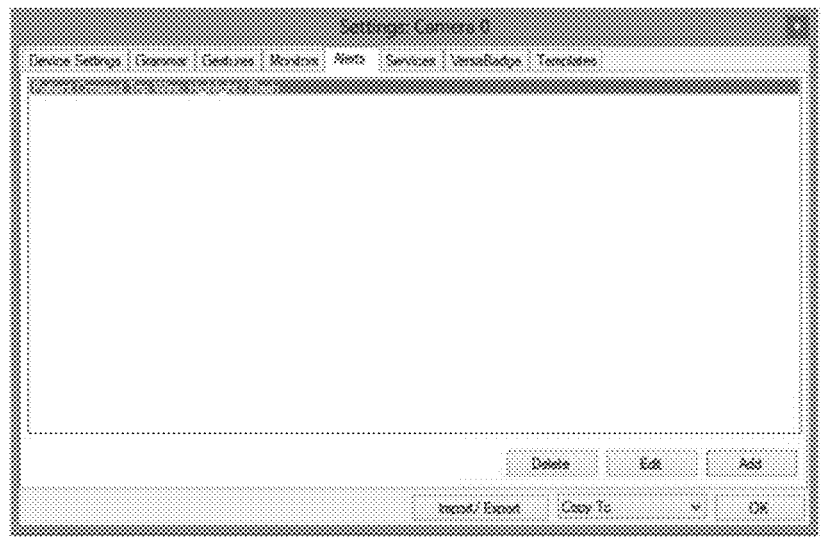

As seen in FIG. 12, once the Event type is selected, under the Action field, the user can select the Action he or she wishes to have the system perform when the selected Event is detected. Once the Event and Action have be selected the OK button (See FIG. 13) is can be selected to save the selected entries.

For certain Actions an additional field may need to be completed to finish the Action. If the field is required, it can appear below the Action dropdown (See FIG. 14). If no further fields are required, the Configure Alert box can display N/A (See FIG. 13) or just be blank. As mentioned above, once all settings are selected, the user clicks or otherwise selects the OK button, which causes the new Alert to be listed in the Alerts tab window. To edit an existing Alert, the user first clicks on or otherwise selects the Alert and then selects the Edit button (See FIG. 15). To delete an Alert, first highlight it can then click on the Delete button (See FIG. 15).

To add more Alerts, the user clicks or selects the Add button and repeats the above described steps. Once finished, the user clicks on or otherwise selects the bottom corner OK button to save and close the window.

Figure 16:
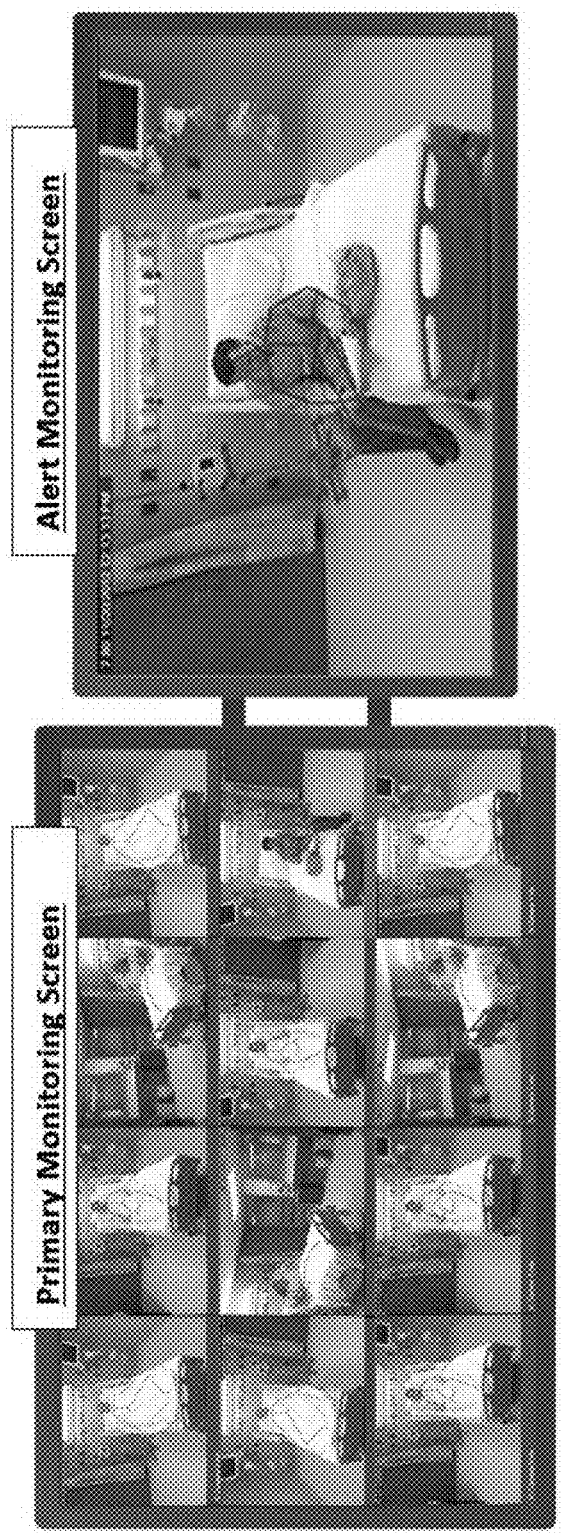
FIG. 16 is a non-limiting example of a centralized video monitoring system that can be used with the system and method shown in FIG. 1.

FIG. 16 shows a non-limiting example of a centralized video monitoring system that can be used with the system and method. The window highlighted in red is a non-limiting example of an alert that can be generated when the patient fails to return to within the perimeter of the virtual safety rails.

The above described system uses several components, including, but not limited to:
1. One or more 3D Camera, Motion and/or Sound Sensors. However, it also within the scope of the invention to eliminate the sound sensor and have the functions of the invention be performed with only motion/camera functions;
2. A Computerized Virtual Safety Rail Monitoring System in electronic communication with the one or more 3D Camera, Motion and Sound sensors;
3. A Computerized Communication System in electronic communication with the Computerized Virtual Safety Rail Monitoring System;
4. A Centralized Monitoring Station in electronic communication with the one or more 3D Camera, Motion and Sound sensors, Computerized Virtual Safety Rail Monitoring System and/or Computerized Communication System;
5. A Centralized Monitoring Primary Display in electronic communication with one or more Centralized Monitoring Stations;
6. A Centralized Monitoring Alert Display in electronic communication with one or more Centralized Monitoring Stations; and/or
7. Database The various components can be in electrical, wired and/or wireless communication with each other.

The automatic detection of an individual leaving a prescribed virtual perimeter will provide significant administrative and clinical benefits to caregivers and individuals alike, including the following non-limiting public benefits:
1. Automation of determination of perimeter violation and automated notification of caregivers or other designated entities.
2. Ability to alert patients and caregivers in time to prevent patient from getting out of bed
3. Reduction in response time for individuals who have fallen and require assistance.
4. Increased survival rate for individuals who have experienced a fall
5. Reduction in costs for hospitalization and medical care related to complications from a fall
6. Ability to distinguish multiple individuals and prevent false positives
7. Ability to distinguish direction of motion of prevent false positives
8. Ability to provide video feed of patient under all lighting conditions to the central video monitoring system
9. Audio and gesture based recognition to allow multiple forms of communication with patient.

Any computer/server/electronic database system (collectively "Computer System") capable of being programmed with the specific steps of the present invention can be used and is considered within the scope of the disclosure. Once programmed such Computer System can preferably be considered a special purpose computer limited to the use of two or more of the above particularly described combination of steps (programmed instructions) performing two or more of the above particularly described combination of functions.

All components of the described system and their locations, electronic communication methods between the system components, electronic storage mechanisms, electronic notification technologies, etc. discussed above or shown in the drawings, if any, are merely by way of example and are not considered limiting and other component(s) and their locations, electronic communication methods, electronic storage mechanisms, electronic notification technologies, etc. can be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the system and method have been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A method for detecting when a monitored individual or any part of the monitored individual has crossed outside of a designated electronic perimeter, said method comprising the steps of:
   (a) electronically calibrating virtual safety rails defining a designated electronic perimeter within an area of a room;
   (b) configuring one or more 3D camera, motion and sound sensors to recognize a specific individual using one or more biometric identifiers of the individual in order to monitor movements of the specific individual;
   (c) electronically receiving a continuous video feed by a computerized monitoring system from the one or more 3D camera, motion and sound sensors located in the room; and
   (d) electronically alerting a computerized communication system when the computerized monitoring system detects that the specific individual located in the room or any part of the specific individual has crossed over the designated electronic perimeter based on 3D information from the continuous video feed received from the one or more 3D camera, motion and sound sensors.

2. The method for detecting of claim 1 wherein the one or more biometric identifiers include distance between points on a body of the specific individual.

3. The method for detecting of claim 1 further comprising the step of electronically issuing an audible message to the individual by the computerized communication system to inform the individual that they have crossed the designated electronic perimeter.

4. The method for detecting of claim 1 further comprising the step of generating an alert on a central video monitoring system if the individual fails to return within the designated electronic perimeter within a predetermined period of time after first issuing an audible message to the individual to return within the electronic perimeter of the virtual safety rails.

5. The method for detecting of claim 1 further comprising the step of notifying a designated person associated with the individual that the individual did not return within the designated electronic perimeter.

6. The method of detecting of claim 2 wherein the computerized monitoring system detects that the designated electronic perimeter has been crossed by the specific individual by tracking skeletal points on the body of the specific individual in real time from the continuous video feed received from the one or more with 3D camera, motion, and sound sensors.

7. A method for detecting when a monitored individual or any part of the monitored individual has crossed outside of a designated electronic perimeter, said method comprising the steps of:
(a) providing one or more 3D camera, motion and sound sensors within a room occupied by a specific individual to be monitored;
(b) configuring the one or more sensors to recognize one or more biometric identifiers of the specific individual in order to monitor movements of only the specific individual;
(c) electronically calibrating virtual safety rails defining a designated electronic perimeter within an area of the room:
(d) electronically forwarding a continuous video feed to a remote computerized monitoring system by the one or more sensors; and
(e) electronically alerting a computerized communication system when the remote computerized monitoring system detects that the specific individual or any part of the specific individual has crossed over the designated electronic perimeter based on 3D information from the continuous video feed received from the one or more 3D camera, motion and sound sensors.

8. The method for detecting of claim 7 further comprising the step of updating a database in communication with the remote computerized monitoring system regarding the detection of the individual or a part of the individual crossing over the designated electronic perimeter.

9. The method for detecting of claim 7 further comprising the step of notifying a previously designated contact by an electronic message informing the previously designated contact of the detected designated electronic perimeter crossing.

10. The method for detecting of claim 7 wherein no electronic alert is provided in step (e) if one or more other persons are detected to be in the room at the time the individual or a part of the individual crosses outside of the designated electronic perimeter though the remote computerized monitoring system continues to receive the continuous video feed from the one or more 3D camera, motion and sound sensors.

11. The method for detecting of claim 7 further comprising the step of continuing to send the video feed from the one or more with 3D camera, motion, and sound sensors to the remote computerized monitoring system after it has been determined that the individual or a part of the individual has crossed outside of the designated electronic perimeter.

12. The method for detecting of claim 7 further comprising the step of electronically issuing an audible message to the individual by the computerized communication system to inform the individual that they have crossed the designated electronic perimeter.

13. The method for detecting of claim 12 wherein the audible message is a pre-recorded message.

14. The method for detecting of claim 13 wherein the pre-recorded message contains the voice of a caregiver associated with the individual.

15. The method for detecting of claim 13, wherein the pre-recorded message advises the individual to return within the designated electronic perimeter defined by the virtual safety rails.

16. The method for detecting of claim 7 further comprising the step of generating an alert on a central video monitoring system if the individual fails to return within the designated electronic perimeter within a predetermined period of time after first issuing an audible message to the individual to return within the electronic perimeter of the virtual safety rails.

17. The method for detecting of claim 16 wherein the alert is an audible alert or a visual alert.

18. The method for detecting of claim 15 further comprising the step of notifying a designated person associated with the individual that the individual did not return within the designated electronic perimeter.

19. The method for detecting of claim 7 wherein the one or more biometric identifiers include distance between points on a body of the specific individual.

20. A method for detecting when a monitored individual or any part of the monitored individual has crossed outside of a designated electronic perimeter, said method comprising the steps of:
(a) providing one or more 3D camera, motion and sound sensors within a room occupied by a specific individual to be monitored;
(b) configuring the one or more sensors to recognize one or more biometric identifiers of the specific individual in order to monitor movements of only the specific individual;
(c) electronically calibrating virtual safety rails defining a designated electronic perimeter within an area of the room;
(d) electronically forwarding a continuous video feed to a remote computerized monitoring system by the one or more sensors; and (e) electronically alerting a computerized communication system when the remote computerized monitoring system detects that the specific individual or any part of the specific individual has crossed over the designated electronic perimeter by tracking skeletal points on a body of the specific individual in real time from 3D information of the continuous video feed received from the one or more 3D camera, motion and sound sensors.

* * * * *